United States Patent
Sarger et al.

(10) Patent No.: US 6,903,817 B2
(45) Date of Patent: Jun. 7, 2005

(54) METHOD FOR OPTICALLY DETECTING CHEMICAL SPECIES CONTAINED IN CONDENSED MEDIA

(75) Inventors: Laurent Sarger, Talence (FR); Philippe Fichot, Begles (FR); Edouard Nau, Bordeaux (FR)

(73) Assignee: Centre National de la Recherche Scientifique - CNRS (FR)

( * ) Notice: Subject to any disclaimer, the term of this patent is extended or adjusted under 35 U.S.C. 154(b) by 0 days.

(21) Appl. No.: 10/725,125

(22) Filed: Dec. 1, 2003

(65) Prior Publication Data

US 2004/0135999 A1 Jul. 15, 2004

Related U.S. Application Data

(63) Continuation of application No. PCT/FR02/01832, filed on May 31, 2002.

(30) Foreign Application Priority Data

Jun. 1, 2001 (FR) .............................................. 01 07216

(51) Int. Cl.[7] .............................................. G01N 21/64
(52) U.S. Cl. .................................... 356/318; 250/458.1
(58) Field of Search ............................... 356/317, 318, 356/417; 250/458.1, 459.1, 461.1, 461.2

(56) References Cited

FOREIGN PATENT DOCUMENTS

| EP | 0 324 583 | 7/1989 |
|---|---|---|
| EP | 0 474 264 | 3/1992 |
| WO | 97/11355 | 3/1997 |

*Primary Examiner*—F. L. Evans
(74) *Attorney, Agent, or Firm*—DLA Piper Rudnick Gray Cary US LLP

(57) ABSTRACT

A method for detecting chemical species present in a condensed medium including determining characteristic wavelengths and intensity values of back-scattered electromagnetic emission signals due to fluorescence of chemical species excited in response to a multiplicity of electromagnetic excitations of distinct wavelengths of at least one chemical species that could be contained in the condensed medium; successively exciting a multiplicity of surface elements of a surface portion of the condensed medium with a laser beam having tunable wavelength capable of taking on at least one of value of the distinct wavelengths of the multiplicity of electromagnetic excitations; successively recording wavelengths and intensity values of the electromagnetic emission signals back-scattered by each of the surface elements in response to the electromagnetic excitations produced by the beam; comparing at least one excitation wavelength and at least one corresponding emission wavelength of the recorded intensity value of the electromagnetic signal back-scattered by each of the surface elements with the determined characteristic intensity value of the back-scattered electromagnetic signal of the chemical species that could be contained in the surface portion; and determining the presence of the chemical species in each of the surface elements when the recorded intensity value of the electromagnetic signal back-scattered by the surface element is greater than a threshold defined at least by the determined characteristic intensity value of the back-scattered electromagnetic signal of the chemical species.

12 Claims, 2 Drawing Sheets

METHOD FOR OPTICALLY DETECTING CHEMICAL SPECIES CONTAINED IN CONDENSED MEDIA

FIELD OF THE INVENTION

This invention pertains to a method and a device for the detection of chemical species present in condensed medium. More particularly, the invention pertains to monitoring the composition of the aqueous effluents discharged by a water purification station or any other industrial operation discharging effluents and monitoring the formation of a chemical compound in an industrial production process.

BACKGROUND

The monitoring of industrial discharges in nature in liquid form is generally performed visually and by analysis of discharged liquid samples according to a specific method for each chemical species being investigated. Furthermore, when monitoring a large expanse of aqueous effluent that might comprise chemical species not uniformly distributed on said expanse, it is necessary to collect multiple samples at different sites in order to localize the origin of the production of said species. The time required for the analysis of the sample and the replacement rate of said effluent affect the diagnosis with regard to this localization.

Moreover, the detection of the appearance of a reaction compound by the collection of samples of the reaction medium present a double drawback. First of all, the reaction is affected by the collection of said sample and, second of all, the longer the time required for the analysis of said chemical compound in relation to the reaction rate and the lower the degree to which the monitoring of the reaction is possible.

In order to resolve this drawback, it has been envisaged to detect the presence of chemical species by spectroscopic means comprising means of electromagnetic excitation oriented to the medium to be analyzed and means for the spectroscopic analysis of the signal back-scattered by the surface of said medium. In this manner, the chemical species are identifiable essentially instantaneously without disturbing the medium.

However, the means of electromagnetic excitation directed on the medium to be analyzed excite a surface of the medium. Thus, on the one hand, the incident signal must be sufficiently strong so as to excite all of the species of the surface and, on the other hand, the means of detection must be extremely sensitive in order to detect the spectra of said chemical species of said surface.

It would therefore be advantageous to provide a method for the detection of chemical species present in a condensed medium which not only makes it possible to precisely detect the nature of the chemical species present in said condensed medium with less costly detection means, but also which enables excitation of the surface of said condensed medium with means of reduced power and thus equally less costly.

SUMMARY OF THE INVENTION

This invention relates to a method for detecting chemical species present in a condensed medium including determining characteristic wavelengths and intensity values of back-scattered electromagnetic emission signals due to fluorescence of chemical species excited in response to a multiplicity of electromagnetic excitations of distinct wavelengths of at least one chemical species that could be contained in the condensed medium; successively exciting a multiplicity of surface elements of a surface portion of the condensed medium with a laser beam having tunable wavelength capable of taking on at least one of the distinct wavelengths of the multiplicity of electromagnetic excitations; successively recording wavelengths and intensity values of the electromagnetic emission signals back-scattered by each of the surface elements in response to the electromagnetic excitations produced by the beam; comparing at least one excitation wavelength and at least one corresponding emission wavelength of the recorded intensity value of the electromagnetic signal back-scattered by each of the surface elements with the determined characteristic intensity value of the back-scattered electromagnetic signal of the chemical species that could be contained in the surface portion; and determining the presence of the chemical species in each of the surface elements when the recorded intensity value of the electromagnetic signal back-scattered by the surface element is greater than a threshold defined at least by the determined characteristic intensity value of the back-scattered electromagnetic signal of the chemical species.

This invention also relates to an apparatus for detecting chemical species present in a condensed medium including means for determining characteristics wavelengths and intensity values of back-scattered electromagnetic emission signals in response to a multiplicity of electromagnetic excitations of distinct wavelengths of at least one chemical species that could be contained in the condensed medium; a laser generator producing a laser beam to successively excite a multiplicity of surface elements of a surface portion of the condensed medium according to wavelengths capable of taking on at least the values of the distinct wavelengths of the multiplicity of electromagnetic excitations; means for successively recording the wavelengths and intensity values of electromagnetic emission signals back-scattered by each of the surface elements in response to the electromagnetic excitations produced by the beam; comparison and determination means for comparing at least one excitation wavelength and at least one corresponding emission wavelength the recorded intensity value of the electromagnetic signal back-scattered by each of the surface elements to the determined characteristic intensity value of the back-scattered electromagnetic signal of the chemical species that could be contained in the condensed medium and for determining the presence of the chemical species in each of the surface elements when the recorded intensity value of the electromagnetic signal back-scattered by the surface elements is greater than a threshold defined at least by the determined characteristic intensity value of the back-scattered electromagnetic signal of the chemical species; and a computer connected to the recording means which has a memory capable of storing simultaneously the wavelength of the back-scattered signals and its intensity for sequential archiving, surface element by surface element, indexed by the displacement means and stored in the memory of the computer the measurements of intensity and wavelengths of the back-scattered signals.

BRIEF DESCRIPTION Of THE DRAWINGS

Other specific characteristics and advantages will become apparent from the description below of specific modes of implementation of the invention presented in a nonlimitative indicative manner with reference to the attached drawings in which.

DETAILED DESCRIPTION

Figure 1:
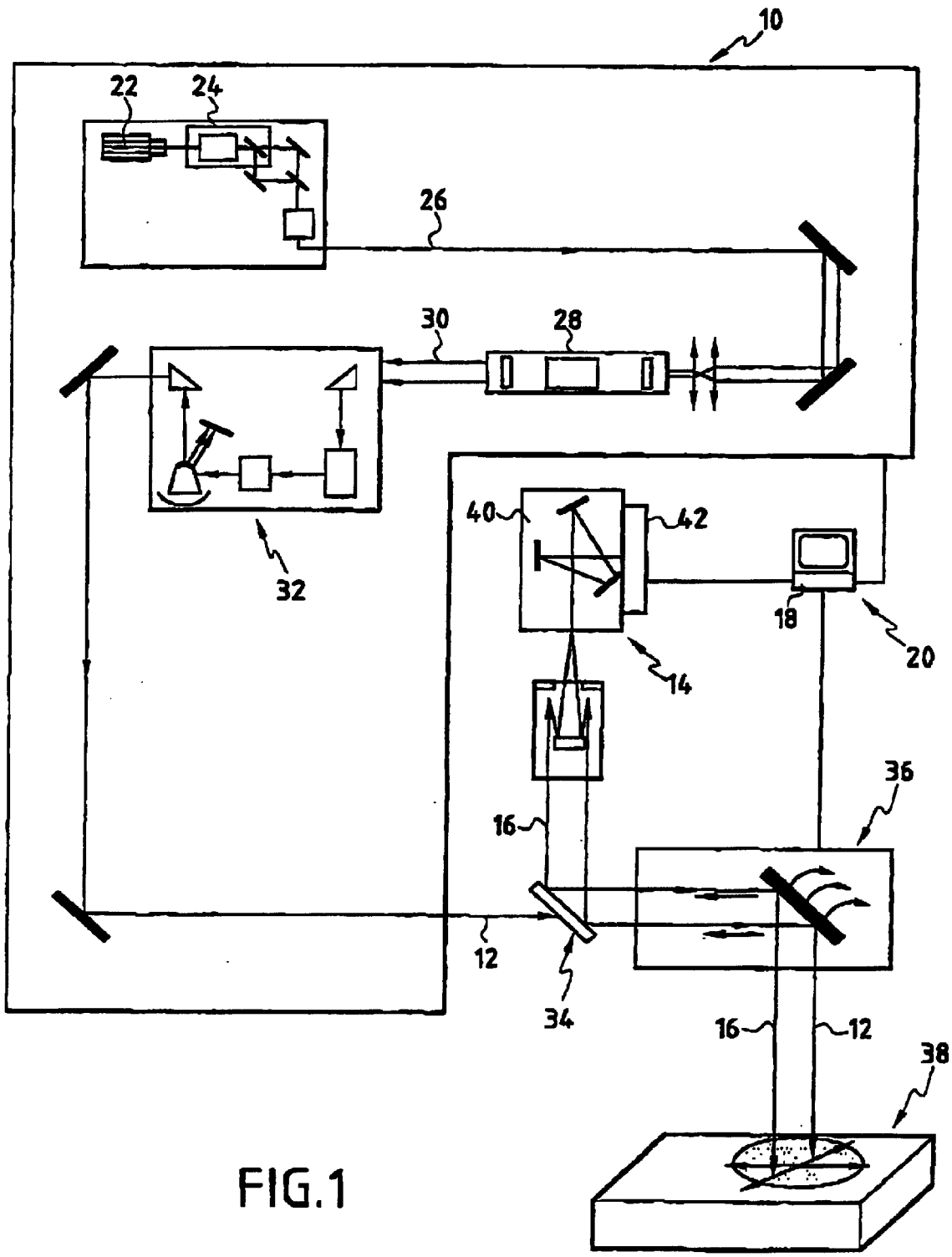
FIG. 1 is a schematic view showing the detection device according to the invention.

The invention provides a method for the detection of chemical species comprising the following steps: determining the characteristic wavelengths and intensity values of back-scattered electromagnetic signals in response to a multiplicity of electromagnetic excitations of distinct wavelengths, of at least one chemical species which can be contained in said condensed medium; successively exciting a multiplicity of surface elements of a portion of the surface of said condensed medium with a laser beams, the tunable wavelength of which can take on at least the values of said distinct wavelengths of said multiplicity of electromagnetic excitation; successively recording the wavelengths and intensity values of the electromagnetic emission signals back-scattered by each of said surface elements in response to the electromagnetic excitations produced by said beam; comparing at least one excitation wavelength and at least one corresponding emission wavelength the recorded intensity value of said back-scattered electromagnetic signal of each of said surface elements at said characteristic intensity value determined from said back-scattered electromagnetic signal of said chemical species which could be contained in said surface portion; and determining the presence of said chemical species in each of said surface elements when said recorded intensity value of said electromagnetic signal back-scattered by said surface element is greater than a threshold defined at least by said given characteristic intensity value of said back-scattered electromagnetic signal of said chemical species.

Thus, the method is based on the analysis of back-scattered electromagnetic signals stemming from the fluorescence of chemical species excited by a beam from laser means, said signals being characteristic of said chemical species. At given excitation wavelengths of the laser beam, the targeted chemical species diffuse the electromagnetic signals, the intensities and wavelengths of which are characteristic of said species. In this manner, by exciting a given chemical species with laser means and by varying the excitation frequency one obtains in response back-scattered signals the wavelengths and intensities of which are characteristic.

When one determines the characteristic wavelengths and intensities of back-scattered signals associated with one or more incident wavelengths determined for a given chemical species, the method according to the invention enables detection of the presence of said given chemical species on a portion of the surface of the more or less extended condensed medium by decomposing said surface portion into surface elements and by exciting said surface element with a laser beam at said given incident wavelengths and back-scattered signal intensities recorded at the characteristic wavelengths and intensities of the signals of said species. In this manner, the laser beam can be applied directly on the surface of the condensed medium and its intersection with said surface determines said surface element. When the wavelengths and the intensity values coincide or if the wavelengths coincide and the intensities are greater than a given threshold, said species is considered to be contained in the condensed medium that has been excited. Quite obviously, the threshold value is adjusted as a function of the noise level of the detector system. The surface elements of an entire surface portion are therefore capable of being analyzed independently from each other with a high level of precision because the laser beam is concentrated on a surface element of a surface portion and one records the wavelengths and the intensity values of the signals back-scattered by said surface element. In this manner, the power of the laser means can be reduced and the detection means can be less sensitive while still preserving a high level of detection.

As a result of the directivity of the laser means, the compounds of the surface elements are excited successively and for each surface element the wavelength of the incident radiation is made to vary and the back-scattered signals are collected so as to establish the presence or lack thereof of the given chemical species in all of the surface elements of said surface portion.

However, as will be explained in greater detail below in the continuation of the description, a chemical species can have multiple characteristic emission signals at different wavelengths in response to a single excitation wavelength. In this case, the incident radiation can be tuned solely on this excitation wavelength if only this chemical species is being investigated.

One records successively the direction of said beams of the laser means advantageously for each surface element of said surface portion so as to establish the reference point coordinates of the origin of said back-scattered electromagnetic emission signals, by means of which one obtains the position of said chemical species in said surface portion. In fact, since the distance that separates the laser means from the surface portion is known, the relative positions of each surface element are determined by the relative angular offsets of the direction of the beams if the laser means pivot around a fixed point. Thus, there is assigned to each given position corresponding to a surface element said back-scattered electromagnetic emission signals corresponding to this surface element in a manner such as to establish the coordinates of the position of said chemical species.

According to a particularly advantageous implementation of the invention, one moreover determines the concentration of said chemical species present in said medium by measuring the quantity of energy emitted by said back-scattered electromagnetic emission signals. In this manner, because for a given wavelength the energy of the back-scattered signal is a function of the number of photons emitted and thus a function of the quantity of chemical species that diffuses the incident radiation, it is possible—after calibration—to correlate the energy of the back-scattered signal and the quantity of said chemical species.

According to a preferred mode of implementation of the invention, one records in parallel the intensity values of said back-scattered electromagnetic emission signals and their corresponding wavelength is recorded as well. In this manner, it is possible to very rapidly record the spectra of the chemical species present in the surface portion.

Thus, for each surface element containing the chemical species that emits a back-scattered signal, the position and the intensity of said signal are detected by detection means simultaneously with the measurement of the wavelength of said signal. Thus, one obtains in a five-dimension base, the position of the surface element with two dimensions, the excitation wavelength, the wavelength of the back-scattered signal and the intensity of said signal. The presence of the chemical species and its position in the surface portion are thereby determined.

The invention provides a device for the detection of chemical species present in a condensed medium. The device comprises: means for determining the characteristic wavelengths and intensity values of back-scattered electromagnetic emission signals in response to a multiplicity of electromagnetic excitations of distinct wavelengths of at least one chemical species that could be contained in said condensed medium; laser means producing a beam for successively exciting a multiplicity of surface elements of a surface portion of said condensed medium according to wavelengths capable of taking at least the values of said distinct wavelengths of said multiplicity of electromagnetic excitations; means for successively recording the wavelengths and the intensity values of electromagnetic emission signals back-scattered by each of said surface elements in response to the electromagnetic excitations produced by said beam; and comparison and determination means for comparing at least one excitation wavelength and at least one corresponding emission wavelength the recorded intensity value of said electromagnetic signal back-scattered by each of said surface elements at said given characteristic intensity value of said back-scattered electromagnetic signal of said chemical species that could be contained in said condensed medium and for determining the presence of said chemical species in each of said surface elements when said recorded intensity value of said electromagnetic signal back-scattered by said surface elements is greater than a threshold defined at least by said given characteristic intensity value of said back-scattered electromagnetic signal of said chemical species.

Thus, a characteristic of the device is based on the combination of the means producing a coherent electromagnetic beam oriented to a surface element of said surface portion at given wavelength values and means for recording the intensity and wavelength values of the back-scattered signals, these means being combined in turn with comparison and determination means, which compare said recorded values with given wavelength and intensity values of the chemical species that could be contained in the condensed medium in order to determine the presence or lack thereof of said species.

According to a particular mode of implementation of the invention, said laser means comprises: a pump laser associated with a frequency doubler; and a parametric oscillator to which said pump laser is coupled in a manner to emit radiation the tunable wavelength of which is in the range between 200 and 800 nm. In this manner, a large number of chemical species can be identified and distinguished from each other.

According to a particular advantageous characteristic, said laser means producing a beam comprises orientation means of said beam for exciting said multiplicity of surface elements of said surface portion of said condensed medium in a manner to analyze the back-scattered electromagnetic emission signals stemming from each of said surface elements and of determining the presence of at least one of said chemical species in each of said surface elements of said surface portion.

As will be explained in greater detail in the continuation of the description, the displacement means comprises mobile mirrors for orienting the beam of each of the surface elements, with these displacement means being controlled by control means.

As a result of the determined position of said mirrors, it is possible to determine the direction of the beam and in a preferential manner the device according to the invention comprises means for successively recording the direction of said beam of the laser means for each surface element of said surface portion so as to reference the coordinates of the origin of said back-scattered electromagnetic emission signals by means of which one obtains the position of said chemical species in said surface portion. In this manner, the surface element by surface element sequential archiving enables creation of a matrix comprising at each point the spectrum of said chemical species.

In a particularly advantageous manner, the detection device comprises recording means comprising a spectrometer coupled to a photodetector matrix in a manner such as to record in parallel the intensity values of said back-scattered electromagnetic emission signals and to record their corresponding wavelength.

Figure 2:
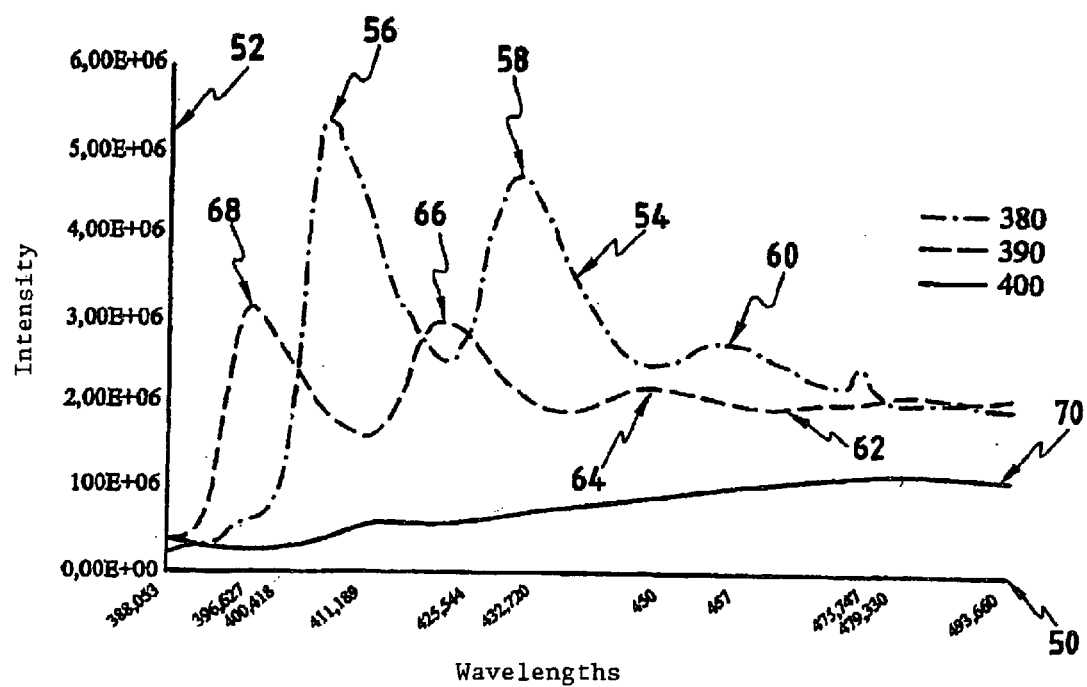
FIG. 2 is a representation of a spectrum which could be obtained by means of the device according to the invention.

Other specific characteristics and advantages will become apparent from the description below of specific modes of implementation of the invention presented in a nonlimitative indicative manner with reference to the attached drawings in which:

FIG. 1 is a schematic view showing the detection device according to the invention;

FIG. 2 is a representation of a spectrum which could be obtained by means of the device according to the invention.

Turning now to drawings, FIG. 1 illustrates the detection device according to the invention which has laser means 10 forming an excitation beam 12, means 14 for recording a back-scattered signal 16 and comparison and determination means 18 contained in the central unit of a computer 20. Moreover, the central unit comprises programs for controlling the entirety of the device according to the invention.

The laser means 10 comprises a pulsed laser 22 of the NdYAG type coupled to a frequency converter unit 24, for examples a frequency doubler or tripler such that the first beam 26 stemming from it is directed to an optical parametric oscillator 28 providing at least one second beam 30 which is directed to a second frequency doubler 32. The parametric oscillator 28 makes it possible to vary in a continuous manner the wavelength of the second beam 30.

In a particularly advantageous manner, said laser means comprises a pumping source operating in femtosecond mode and forming a compact system. These laser means have the advantage of being available at low cost.

The tunable laser means 10 enables provision of an excitation beam 12 with a section of several $cm^2$ at a distance of 100 m and the wavelength of which can vary at least between 220 and 750 nm, wavelength interval within which the chemical species that could be excited have characteristic spectra.

The pump laser 22 can be advantageously replaced by a diode system that has the same advantages.

The excitation beam 12, originating from said laser means 10, traverses semitransparent means 34, for example, a semitransparent prism or strip, and then encounters means 36 for the displacement of the excitation beam 12 constituted by two orientable mirrors which reflect the beam onto a condensed medium 38 that could contain the chemical compounds. In this manner, the intersection of the excitation beam and the surface of the condensed medium form at 100 m of distance a surface element of several $cm^2$, for example, 3 $cm^2$.

Such chemical compounds can emit a back-scattered electromagnetic signal 16 in response to the excitation induced by the excitation beam 21, said back-scattered electromagnetic signal 16 prints the same optical path as the excitation beam 12 up to the transparent means 34 that orient the back-scattered signal 16 to the recording means 14.

The recording means 14 comprises a spectrometer 40 capable of determining the wavelengths of the back-scattered electromagnetic signals 16 and coupled to detector means 42 constituted by a matrix of photoelectric sensors, for example, CCD, capable of determining the intensities at a position of the back-scattered signals 16. Moreover, the recording means 14 are linked to the center unit of the computer 20 which has a memory that can store simultaneously, notably, the wavelength of the back-scattered signal 16 and its intensity.

The central unit of the computer 20 is also linked to the laser means and to the means 36 for displacement of the excitation beam so as to be able to control them by means of command programs. Furthermore, the direction of the excitation beam 12 which determines the position of an excited surface element is also stored in the memory of the computer 20 along with the intensities and wavelengths of the back-scattered waves. According to a particular mode of implementation of the invention, the position of the surface elements can be determined by referencing the coordinates of the pixels of the photoelectric sensor pixels which is located in the focal plane of the optical system.

In this manner, the computer 20 can control for a given position of the means 36 for displacement of the excitation beam 12, the laser means 10 in a manner such as to vary as a function of time the wavelength of the excitation beam 12, for example, between 250 and 450 nm. The computer 20 simultaneously stores in its memory the determined position of the back-scattered signal 16, determined by the means 36 for displacement of the beam, the wavelength and back-scattered signal intensity 16 for each of the wavelength values of the excitation beam 12. The command programs then command the movement of the displacement means 36 in a manner such that the excitation beam 12 targets the surface element of the surface portion 38 contiguous to the preceding so as to perform the same spectral scanning. This operation is repeated so as to cover the entire surface portion 38.

Thus, five variables are stored in the memory space of the computer 20: three variables characterize the chemical species present in the surface element that the excitation beam 12 excites and two variables characterize the position of said surface element in relation to the surface elements whose coordinates are referenced by the relative positions of the displacement means 36 and stored in the memory of the computer 20.

The characterization of the chemical species will be described with reference to the means of FIG. 2 illustrating the spectra of a mixture containing at least two aromatic hydrocarbons: anthracene and a benzopyrene.

The spectrum of the chemical species is characterized by the variable wavelength of the back-scattered signal 16 plotted on the abscissa axis 50 and by the variable intensity of the back-scattered signal plotted on the ordinate axis 52. Curve 54 represents the intensity of the back-scattered signals and their wavelength in response to an excitation with a wavelength of 380 nm. Curve 54 exhibits three peaks 56, 58, 60 at 411, 437 and 457 nm, respectively, characteristic of benzopyrene. Curve 62, in response to an excitation at 390 nm, also exhibits three peaks, 64, 66 and 68 at 450, 425 and 396 nm, respectively, characteristic of anthracene. Furthermore, the excitation at 400 nm generates an essentially flat curve 70 which does not allow any characterization.

Looking at these curves 54, 62, 70, it can be understood that the detection of a given chemical species, for example, anthracene, in a given condensed medium, can be performed by comparing the intensity of the signal back-scattered at 411, 432 and 457 u for an excitation produced at 390 nm and determining in it the presence of anthracene if, for example, the intensity of the signals at all the wavelengths is proportional to the intensity of the characteristic signals of anthracene.

In contrast, it can be understood that an excitation at 400 nm of the condensed medium does not allow distinction of the presence of anthracene nor that of benzopyrene.

Very clearly, the spectra of the chemical species, made concrete by the intensity and emission wavelength of the emission signals back-scattered in response to the excitation signals are determined either by calculation or, preferably, by experimentation and are stored in databases in the memory of the computer 20.

As has been shown with anthracene, it is not necessary to compare the set of the spectrum, which forms a determined surface in space, of excitation wavelength, emission wavelength and intensity of the emitted signal, in order to determine the presence of the chemical species under consideration but rather simply to carefully select the characteristic excitation/emission wavelengths and to compare the intensity of the emission signals.

Nevertheless, when a large number of chemical species could be present in the condensed medium and the goal is to detect them, it is advantageous to proceed to the comparison of a larger portion of the spectrum length of wave by wavelength.

The identification of a given chemical species can be performed by comparison of the recorded spectrum with the spectrum of said chemical species stored in the databases by means of any known identification program.

A characteristic of the device according to the invention is based on the sequential archiving, surface element by surface element, indexed by displacement means 36 and stored in the memory of the computer 20, of the measurements of intensity and wavelength of the back-scattered signals. Thus, the three variables are stored with two localization variables characterized by the relative directions of the beam of the laser means. In this manner, and taking into account the acquisition rates of the different signals, from each scanning of said surface element after scanning of all of the others, it is possible to detect the presence or lack thereof of the chemical species under consideration and possibly its displacement, by displaying the variable spectrum intensity for the contiguous surface element or element.

Each chemical species exhibits different durations of fluorescent life. Thus, by collecting the fluorescence emissions at clearly determined times after excitation, it is possible to minimize the interference between the fluorescence signal and the very short-term emissive phenomena.

In this manner, in order to evaluate the evolution over time of the spectrum of the investigated space, one measures the fluorescence intensity of each species after a certain delay or during a determined time interval, after synchronization of the excitation signal and the detector.

Thus, one advantageously determines the characteristic emission values of back-scattered electromagnetic emission signals, in response to an excitation after a given delay and during a given time interval of at least one chemical species that could be contained in said condensed medium; one records the intensity values of the back-scattered electromagnetic emission signals in response to an excitation of said condensed medium after said given time delay and during said period of time; and one compares said recorded intensity values and said determined intensity values in a manner such as to determine the presence of said chemical species in said condensed medium.

In this manner, the time-related resolution of the fluorescence signal makes it possible to discriminate among the different chemical species as a function of the duration of life of their fluorescence emission.

The detection device according to the invention can be installed above water flows or rivers into which industrial operations discharge their effluents in order to continuously monitor the nature of the discharged effluents and to determine whether the toxic chemical species that they could produce are directly discharged into the environment.

Other envisaged applications make it possible, for example, to follow the dynamic evolution of events taking place in a living cell. The chemical constituents that the cell produces, such as proteins, can be characterized by fluorescence and thus by determined spectra. Consequently, the appearance of a given protein, for example, can be detected by the device according to the invention.

Obviously, the optical system positioned between the recording means, notably the detector, and the condensed medium to be explored, is completely different when one visualizes a surface portion the dimension of which are on the order of hundred of meters and when the exploration is directed at a surface portion of a living cell.

What is claimed is:

1. A method for detecting chemical species present in a condensed medium comprising:
    determining characteristic wavelengths and intensity values of back-scattered electromagnetic emission signals due to fluorescence of chemical species excited in response to a multiplicity of electromagnetic excitations of distinct wavelengths of at least one chemical species that could be contained in said condensed medium;
    successively exciting a multiplicity of surface elements of a surface portion of said condensed medium with a laser beam having tunable wavelength capable of taking on at least one of value of said distinct wavelengths of said multiplicity of electromagnetic excitations;
    successively recording wavelengths and intensity values of the electromagnetic emission signals back-scattered by each of said surface elements in response to the electromagnetic excitations produced by said beam;
    comparing at least one excitation wavelength and at least one corresponding emission wavelength of the recorded intensity value of said electromagnetic signal back-scattered by each of said surface elements with said determined characteristic intensity value of said back-scattered electromagnetic signal of said chemical species that could be contained in said surface portion; and
    determining the presence of said chemical species in each of said surface elements when said recorded intensity value of said electromagnetic signal back-scattered by said surface element is greater than a threshold defined at least by said determined characteristic intensity value of said back-scattered electromagnetic signal of said chemical species.

2. The method according to claim 1, further comprising exciting the surface element of the condensed medium with a laser beam and varying the excitation frequency for a given chemical species in a manner to enable detection of the presence of said chemical species on a portion of the surface of the condensed medium, the laser beam stemming from a laser generator being concentrated on a surface element on a surface portion.

3. The method according to claim 1, wherein successively recording comprises observing the direction of said laser beam for each surface element of said surface portion to reference coordinates of origin of said back-scattered electromagnetic emission signals by which the position of said chemical species in said surface portion is obtained.

4. The method according to claim 1, further comprising determining the concentration of said chemical species present in said medium by measuring the amount of energy emitted by said back-scattered electromagnetic emission signals.

5. The method according to claim 1, further comprising recording in parallel intensity values of said back-scattered electromagnetic emission signals and recording their corresponding wavelength.

6. The method according to claim 1, further comprising:
    determining characteristic intensity values of the back-scattered electromagnetic emission signals in response to an excitation after a given interval of time and during a given period of time of at least one chemical species that could be contained in said condensed medium;
    recording intensity values of the back-scattered electromagnetic emission signals in response to an excitation of said condensed medium after said given interval of time and during said given period of time; and
    comparing said recorded intensity values and said determined intensity values to determine the presence of said chemical species in said condensed medium.

7. Apparatus for detecting chemical species present in a condensed medium comprising:
    means for determining characteristic wavelengths and intensity values of back-scattered electromagnetic emission signals in response to a multiplicity of electromagnetic excitations of distinct wavelengths of at least one chemical species that could be contained in said condensed medium;
    a laser generator producing a laser beam to successively excite a multiplicity of surface elements of a surface portion of said condensed medium according to wavelengths capable of taking on at least the values of said distinct wavelengths of said multiplicity of electromagnetic excitations;
    means for successively recording the wavelengths and intensity values of electromagnetic emission signals back-scattered by each of said surface elements in response to the electromagnetic excitations produced by said beam;
    comparison and determination means, for comparing at least one excitation wavelength and at least one corresponding emission wavelength the recorded intensity value of said electromagnetic signal back-scattered by each of said surface elements to said determined characteristic intensity value of said back-scattered electromagnetic signal of said chemical species that could be contained in said condensed medium and for determining the presence of said chemical species in each of said surface elements when said recorded intensity value of said electromagnetic signal back-scattered by said surface elements is greater than a threshold defined at least by said determined characteristic intensity value of said back-scattered electromagnetic signal of said chemical species; and
    a computer connected to the recording means which has a memory capable of storing simultaneously the wavelength of the back-scattered signals and its intensity for sequential archiving, surface element by surface element, indexed and stored in the memory of the computer the measurements of intensity and wavelengths of the back-scattered signals.

8. The apparatus according to claim 7, wherein the laser generator comprises:

a pump laser associated with a frequency doubler; and a parametric oscillator to which said pump laser is coupled to emit radiation and having a tunable wavelength between 200 and 800 nm.

9. The apparatus according to claim 7, wherein the laser generator comprises a pumping source operating in femtosecond mode.

10. The apparatus according to claim 7, wherein said laser generator comprises means for orientation of said beam for exciting said multiplicity of said surface elements of said surface portion of said condensed medium to analyze the back-scattered electromagnetic emission signals originating from each of said surface elements and of determining the presence of at least one of said chemical species in each of said surface elements of said surface portion.

11. The apparatus according to claim 10, further comprising means for successively recording the direction of said laser beam for each surface element of said surface portion to reference the coordinates of the origin of said back-scattered electromagnetic emission signals such that one obtains the position of said chemical species in said surface portion.

12. The apparatus according to claim 7, wherein the recording means comprises a spectrometer coupled to a matrix of photodetectors to record in parallel the intensity values of said back-scattered electromagnetic emission signals and to record their corresponding wavelengths.

* * * * *